(12) United States Patent
Gershenson

(10) Patent No.: US 11,650,180 B2
(45) Date of Patent: May 16, 2023

(54) ELECTROMAGNET FOR A THERMOGRAPHY SYSTEM

(71) Applicant: Meir Gershenson, Cholul Yucatan (MX)

(72) Inventor: Meir Gershenson, Cholul Yucatan (MX)

( * ) Notice: Subject to any disclaimer, the term of this patent is extended or adjusted under 35 U.S.C. 154(b) by 0 days.

(21) Appl. No.: 17/890,328

(22) Filed: Aug. 18, 2022

(65) Prior Publication Data

US 2022/0397554 A1 Dec. 15, 2022

Related U.S. Application Data

(62) Division of application No. 17/403,886, filed on Aug. 17, 2021, now Pat. No. 11,422,112.

(60) Provisional application No. 63/123,891, filed on Dec. 10, 2020.

(51) Int. Cl.
| | |
|---|---|
| H05B 6/36 | (2006.01) |
| G01N 27/90 | (2021.01) |
| H01F 7/06 | (2006.01) |
| H01F 7/20 | (2006.01) |
| G01N 25/72 | (2006.01) |
| G06T 7/00 | (2017.01) |

(52) U.S. Cl.
CPC ............ *G01N 27/9006* (2013.01); *H01F 7/06* (2013.01); *H01F 7/206* (2013.01); *H05B 6/365* (2013.01); *G01N 25/72* (2013.01); *G06T 7/0004* (2013.01); *G06T 2207/10048* (2013.01)

(58) Field of Classification Search
CPC ................................ H01F 7/20; H05B 6/365; G01N 25/00–25/72
USPC ......... 336/181, 184, 187, 212, 214–217, 221
See application file for complete search history.

(56) References Cited

U.S. PATENT DOCUMENTS

2004/0032315 A1  2/2004  Illingworth
2020/0358317 A1  11/2020  Richter

FOREIGN PATENT DOCUMENTS

| DE | 102012008531 B4 * | 2/2014 | ............ G01N 25/72 |
|---|---|---|---|
| GB | 2115230 | 9/1983 | |
| WO | WO-2018189209 | 10/2018 | |

OTHER PUBLICATIONS

International search report for PCT Application No. PCT/US2021/43358 dated Nov. 15, 2021.
He, Min, et al., "Investigation on a new inducer of pulsed eddy current thermography." AIP Advances 6.9 (2016), p. 095221, https://doi.org/10.1063/1.4963894.
Zhiping, Liu, et al., "Design and experimental study of a novel excitation coil based on pulsed eddy current thermography." Insight-Non-Destructive Testing and Condition Monitoring 59.9 (2017), pp. 491-499.

(Continued)

*Primary Examiner* — Ramon M Barrera
(74) *Attorney, Agent, or Firm* — Pearl Cohen Zedek Latzer Baratz LLP

(57) ABSTRACT

An electromagnet for a thermography system comprising a first elongated magnetic core spaced apart from a second elongated magnetic core; at least a first shorting bar connecting substantially at a first end of the first elongated magnetic core and a first end of the second elongated magnetic core; and at least a first excitation coil configured to conduct electrical current.

3 Claims, 3 Drawing Sheets

(56) References Cited

OTHER PUBLICATIONS

Gorostegui-Colinas, Eider, et al., "Induction thermography-based inspection of EBW and TIG welded Inconel 718 components: steps towards industrialization." Thermosense: Thermal Infrared Applications XLII. vol. p. 11409. International Society for Optics and Photonics, 2020.

Office Action for U.S. Appl. No. 17/403,886 dated Mar. 9, 2022.

\* cited by examiner

ELECTROMAGNET FOR A THERMOGRAPHY SYSTEM

CROSS REFERENCE TO RELATED APPLICATIONS

This application is a Divisional Application of U.S. patent application Ser. No. 17/403,886 filed Aug. 17, 2021 which claims priority of U.S. Provisional Patent Application No. 63/123,891 filed Dec. 10, 2020, which is hereby incorporated by reference.

FIELD OF THE INVENTION

The present invention relates to electromagnets. More particularly, the present invention relates to an electromagnet for a thermography system.

BACKGROUND OF THE INVENTION

Pulse eddy current thermography (PECT) is a method used to detect defects in metal which intercept exposed surface. Using alternate magnetic field, a surface current is produced, which is called eddy current. Eddy currents flow on top of a magnetized surface. If the eddy current flow encounters a surface defect, such as a crack, the eddy current may be diverted. Using a thermal imaging camera, it may be possible to monitor the intensity of the current by the heat it generates. A change in the heat pattern as a result of change in the current flow may be an indication of a flaw. Analyzing the heat pattern may help to characterize the flaw.

Eddy currents used for generating heat are typically produced by an electromagnet fed with high power high frequency generator. Common parameters used in PECT are usually: frequency (e.g., between few kilo Hertz to few hundred kilo Hertz), power (e.g., typically one to two kilowatts) and tune duration (e.g., about of a fraction of a second).

Heating may be produced by sinusoidal magnetic fields. Sinusoidal magnetic fields in turn the produce induced voltage and current. To maximize the induced voltage, it is necessary to maximize the magnetic flux through a sample. The flux may be limited by the geometry of the sample in relation to the coil. Typically, only a fraction of the flux produced by the coil will intercept the test sample. A known method for increasing the coupling of the magnetic field is putting the sample inside the coil. Putting the sample inside the coil might limit the sample size and obstruct the sample from thermal camera.

The ratio of the magnetic flux that passes through the sample relative to the total magnetic flux generated by the coil is marked as k. k ranges from 0 to 1. A low value of k (e.g., approaching a k value of 0) means that only small fraction of the magnetic flux will pass through the sample, reducing the power induced in the sample. Whereas, a high value of k (e.g., approaching a k value of 1) means that a considerable portion of the magnetic flux will through the sample.

A small value of k may also mean that most of the energy in the magnetic field is reactive. Reactive magnetic fields translate to voltage and current at 90 degrees out of phase. Such a reactive component will result in large current flow and internal ohmic loses at the generating circuit. To minimize loses and maximize the magnetic flux passed to the sample, one needs a value of k approaching 1.

Some PECT systems use magnetic excitation coils designed for induction furnaces where magnetic flux is generated by a helical coil. These systems typically suffer the limitations of low coupling coefficient k, non-uniform field and obstructed view of the thermal camera by the coil.

Some improvements to the coupling were achieved by using a single turn coil or flat coil instead of the helical excitation coils. An additional improvement was obtained by use of Helmholtz coil. Helmholtz coil is constructed from two coaxial ring coils of diameter D separated by the same distance D. Helmholtz coils may produce a substantially uniform magnetic field at the center of the Helmholtz coil, while keeping the view unobstructed.)

The limitation of the Helmholtz coils is that only a considerably small portion of the coil has a uniform magnetic field, the coefficient k is small, and the sample has to fit inside the center space of the coil. As a result, Helmholtz coils may be useful for small samples or for a limited section of large elongated objects, but exclude most large objects.

An additional improvement to coupling was achieved by using a high magnetic permeability core with a U-shape. The U-shaped magnetic core allows to concentrate the magnetic field outside the electromagnet by extending the core to the desired location. High permeability materials are commonly used to produce transformers with permeability of few thousand time higher than that of free space. The magnetic cores are designed to have low loses at high frequency and high magnetic saturation. Three forms of magnetic cores for electromagnets were previously used: a U-shaped form, a form of two vertical bars, and a frame form. The U-shaped electromagnet generates large uniform current flow but partially obstructs the view of the thermal camera. The two vertical bars electromagnet enable unobstructed view of the tested object but reduces the produced magnetic field by half. Additionally, the two vertical bars electromagnet produces large alternating magnetic field at the camera location. The alternating magnetic fields at the camera location can produce electromagnetic interference, that might affect the camera. The frame electromagnet is made with two opposing solenoids which are wound on opposites sides of the frame. The frame electromagnet does not obstruct the view, but the winding of the two coils limits the minimum distance between the magnetic cores and the sample. Because of way the coils are winded on the frame electromagnet, the value of k is lowered and the produced current distribution in nonuniform.

It may be desirable to produce an electromagnet for a thermography system that has a high value of k, produces a uniform magnetic field and does not obstruct the view of the thermal camera.

SUMMARY OF THE INVENTION

There is thus provided, in accordance with an embodiment of the invention, an electromagnet for a thermography system includes a first elongated magnetic core spaced apart from a second elongated magnetic core; at least a first shorting bar connecting substantially at a first end of the first elongated magnetic core and a first end of the second elongated magnetic core; and at least a first excitation coil configured to conduct electrical current.

According to some embodiments of the invention, the first shorting bar connects a proximal surface of the first elongated magnetic core and a proximal surface of the second elongated magnetic core.

According to some embodiments of the invention, the first elongated magnetic core is substantially parallel to the second elongated magnetic core.

According to some embodiments of the invention, the first excitation coil is wrapped around the first shorting bar.

According to some embodiments of the invention, the first elongated magnetic core has a substantially flat distal surface and the second elongated magnetic core has a substantially flat distal surface.

According to some embodiments of the invention, the electromagnet comprises a second shorting bar that connects substantially at a second end of the first elongated magnetic core and second end of the second elongated magnetic core.

According to some embodiments of the invention, the second shorting bar connects a proximal surface of the first elongated magnetic core and a proximal surface of the second elongated magnetic core.

According to some embodiments of the invention, a second excitation coil is wrapped around the second shorting bar.

According to some embodiments of the invention, a looping direction of the first excitation coil is opposite to a looping direction of the second excitation coil.

According to some embodiments of the invention, the first excitation coil is wrapped around the first elongated magnetic core along an axis substantially orthogonal to a distal surface of the first elongated magnetic core.

According to some embodiments of the invention, the first excitation coil is wrapped around the second elongated magnetic core along an axis substantially orthogonal to a distal surface of the second elongated magnetic core.

According to some embodiments of the invention, a looping direction of the first excitation coil around the first elongated magnetic core is opposite to a looping direction of the first excitation coil around the second elongated magnetic core.

According to some embodiments of the invention, a portion of the first excitation coil that passes between the first and second elongated magnetic cores is substantially parallel to the first shorting bar.

According to some embodiments of the invention, the first shorting bar connects a first lateral surface of the first elongated magnetic core and a first lateral surface of the second elongated magnetic core.

There is thus provided, in accordance with an embodiment of the invention, a thermography system includes a thermal imaging camera; a frequency generator; and an electromagnet comprising an elongated first magnetic core and an elongated second magnetic core, at least a first shorting bar, and at least a first excitation coil connected to the frequency generator, wherein the first shorting bar connects the first and second magnetic cores substantially at a first end of the first and second magnetic cores.

According to some embodiments of the invention, the first excitation coil is wrapped around the first shorting bar.

According to some embodiments of the invention, the electromagnet further comprises a second shorting bar and a second excitation coil wrapped around the second shorting bar.

According to some embodiments of the invention, the first excitation coil is wrapped around the first magnetic core along an axis substantially orthogonal to a distal surface of the first magnetic core, and wherein the first excitation coil is wrapped around the second magnetic core along an axis substantially orthogonal to a distal surface of the second magnetic core.

According to some embodiments of the invention, the imaging camera is an infra-red camera.

There is thus provided, in accordance with an embodiment of the invention, a method for thermographic imaging using a thermography system includes generating alternating electric current using a frequency generator to induce Eddy current in a sample, the frequency generator connected to a first excitation coil in an electromagnet, the electromagnet comprising an elongated first magnetic core and an elongated second magnetic core, at least a first shorting bar, the shorting bar connecting the first and second magnetic cores substantially at a first end of the first and second magnetic cores; and obtaining thermal images of the sample using a thermal imaging camera.

BRIEF DESCRIPTION OF THE DRAWINGS

In order for the present invention to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
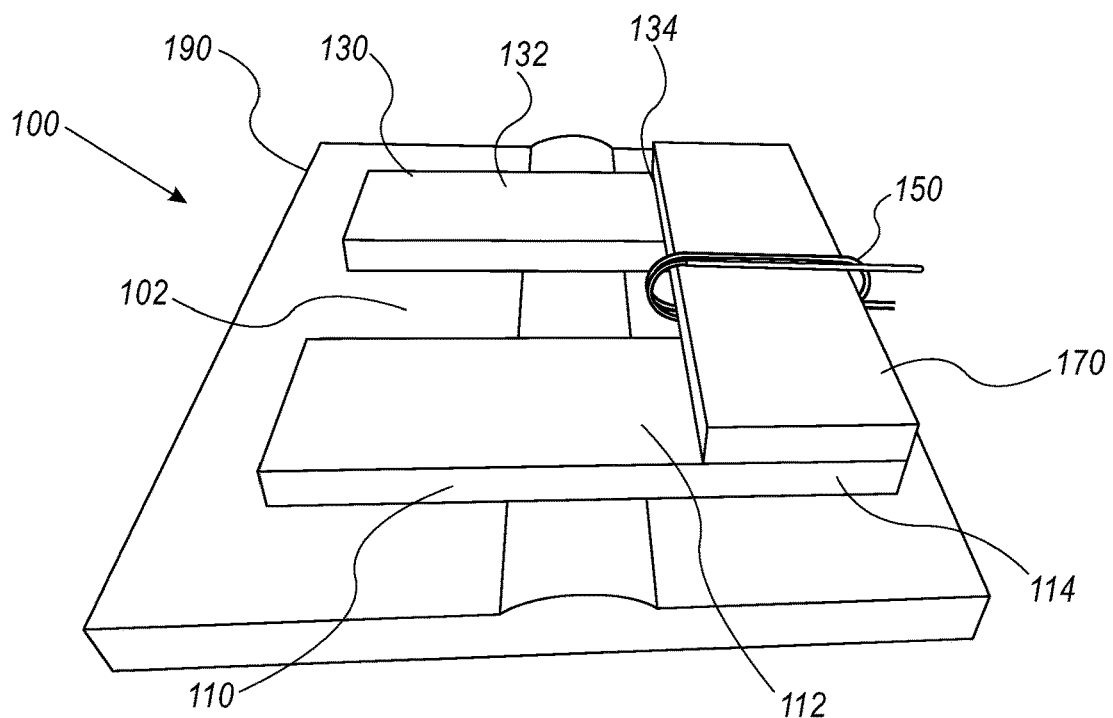
FIG. 1 is an electromagnet for a thermography system with two elongated magnetic cores and a first shorting bar connecting at a first end of the magnetic cores, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

In some embodiments of the present invention, a thermography system may include a frequency generator connected to an electromagnet with an excitation coil and a thermal camera. The frequency generator may generate alternating currents that run through the excitation coil. The alternating currents running though the excitation coil may induce eddy currents in a sample (e.g., metallic sample). The induced eddy currents heat up the sample, and the camera may capture a thermal image of the sample. By analyzing the thermal image of the sample, defects, anomalies and structural deficiencies can be detected. For example, eddy currents induced in a sample with defects may yield a different heat pattern that a sample without defects.

In some embodiments of the present invention, an electromagnet for a thermography system may include a first elongated magnetic core spaced apart from a second elongated magnetic core, and at least a first shorting bar connecting substantially at a first end of the first elongated magnetic core and a first end of the second elongated magnetic core. The magnetic cores and the shorting bar define a structure that conducts a magnetic field induced by an excitation coil. The excitation coil may be wrapped around the shorting bar or the magnetic cores. When current passes through the excitation core, a magnetic field is induced in the shorting bar and magnetic cores. The magnetic field induced in the magnetic bars may in turn induce eddy currents in a sample. The sample may be metallic, as metallic material may manifest eddy currents when an introduced to an alternating magnetic field. The magnetic cores should be placed as close as possible to the sample to maximize the value of k.

In some embodiments of the present invention, the magnetic cores and the shorting bar may comprise of high permeability materials (e.g., the magnetic cores and the shorting bars may be made high permeability materials such as iron or ferrite). Magnetic cores made of high permeability materials may be designed to have low loses at high frequency and high magnetic saturation.

When using high frequency, the induce Eddy currents may be limited flow close to a surface of the sample skin deep). For example, the higher the frequency the closer Eddy currents are to the surface of the sample. As for coils, in coils with large diameter wires at high frequencies, current may flow only at the outer surface of the wire. This in turn might result in reduced effective conductivity and increase losses. To avoid these losses, coils may be made from hollow tubes with wall thickness less than the skin depth of the flowing current. Alternatively or additionally, coils may be made from multiple isolated wires wherein individual wire diameter may be smaller than the skin depth of the flowing current (e.g., litz wires).

Using high permeability materials for the magnetic core, may produce a magnetic field in a region outside the coil that induces uniform eddy current distribution in a sample. High permeability material such as manganese zinc ferrites have very high magnetic permeability in the range from 9000 to 15,0000. Much higher than the permeability of free space which is μ0. In some embodiments of the present invention, it may be applicable to use materials with lower values of u for the magnetic cores, but the performance of the electromagnet may suffer. High μ materials may be commercially available for use, e.g., for construction of transformers, inductors and magnetic shielding.

In some embodiments of the present inventions, using the static magnetic potential may be a good description of the produced magnetic field (e.g., the static magnetic potential description may fit the range of frequencies used for this application). The magnetic field H away from current sources can be written as gradient of a magnetic scalar potential $V_m$:

$$H(r) = \nabla V_m(r)$$

and $$\nabla \mu \nabla V_m(r) = 0$$

H is the magnetic field vector. $V_m$ is given by the Ampere turns of the coil. r is the coordinate. $\nabla V_m(r)$ is the gradient of the magnetic scalar potential according to the coordinate r. μ is the magnetic permeability and $\nabla \mu \nabla V_m(r)$ is the gradient of the magnetic field vector. This equation may be similar to the equations describing steady current in a conductor:

$$\nabla \sigma \nabla V(r) = 0$$

and $$j(r) = \sigma \nabla V(r)$$

V is the electric potential or the voltage and $\nabla V(r)$ is the gradient of the electric potential according to the coordinate r. σ is the conductivity and $\nabla \sigma \nabla V(r)$ is the gradient of the current density. j is current density and j(r) is the current density according to the coordinate r. The second equation describes that the current may be represented as a differential Ohm's law. In a region with very high conductivity, the potential can be approximated by a constant voltage V. The same is true for the magnetic potential $V_m(r)$, the high permeability region, $V_m(r)$ can be approximated as a constant.

Equations used for design of transformers with air gap, may be a good approximation for this application, assisting in designing the eddy current exciter (e.g., the electromagnet and the excitation coil). For a transformer with a magnetic core, the equations describing the magnetic flux are:

$$\Phi = Ni / (R_c + R_g)$$

$$R_c = \frac{l_c}{\mu_c A_c} \quad R_g = \frac{l_g}{\mu_g A_g}$$

Φ is the magnetic flux, N is number of turns, i is current, l is length and A is area of a cross section. Subscript c stands for core, and subscript g for air gap. N i is the static magnetic potential. R is the reluctance. For more complex geometries of air gap, calculation of $R_g$ may be more complicated the equations above may still true be a good approximation.

In some embodiments of the present invention, $R_g$ may be much greater than R (e.g., $R_g >> R_c$). As such, the flux may be determined mainly by the air gap. Increasing the cross section at the gap may also increase the magnetic flux.

A solution to the magnetic field in the vicinity of the high permeability material (e.g., similar to the current near high conductivity electrode in lower conductivity materials such as seawater) may depend on the value of the magnetic potential and the local geometry. Alternatively or additionally, the solution to the magnetic field may be independent of how the potential is generated and/or the geometry away from a solution location. In other words, the shape of the magnetic field near the magnetic core depends very little on the core details far away from that location.

In some embodiments of the present invention, an electromagnet with a magnetic core having a form similar to a U-shape, may induce a substantially uniform current distribution between two magnetic poles of the electromagnet. A first elongated magnetic core and a second elongated magnetic core (e.g., with at least a first connecting shorting bar) may define two magnetic poles. As such, a current distribution induced between the first elongated magnetic pole and the second elongated magnetic pole may be substantially uniform.

In some embodiments of the present invention, the electromagnet may have the first elongated magnetic core spaced apart from the second elongated magnetic core. E.g., a gap may be present between the first elongated magnetic core and the second elongated magnetic core. Induced eddy currents in the gap may be uniformly distributed. Additionally, the gap may provide an unobstructed view for a thermal camera. For example, the area heated with uniform eddy currents (e.g., in the gap) may have an unobstructed view for a thermal camera.

In some embodiments of the present invention, the electromagnet may produce a magnetic field that induces substantially uniform eddy currents in a sample. The electromagnet may be configured to maximize the induction of eddy currents in the sample while minimizing the electromagnetic interference (EMI) emitted to the environment.

FIG. 1 is an electromagnet for a thermography system with two elongated magnetic cores and a first shorting bar connecting at a first end of the magnetic cores, in accordance with some embodiments of the present invention. Electromagnet 100 may comprise first elongated magnetic core 110 and second elongated magnetic core 130. First elongated magnetic core 110 may be spaced apart from second elongated magnetic core 130, so that gap 102 may form between first elongated magnetic core and second elongated magnetic core. Electromagnet 100 may induce substantially uniform eddy currents in sample 190. For example, electromagnet 100 may be configured to induce uniform eddy currents in sample 190 in the area of gap 102.

In some embodiments of the present invention, first shorting bar I/O may connect substantially at first end 114 of first elongated magnetic core 110 and first end 134 of second elongated magnetic core 130. First shorting bar 170 may short first elongated magnetic core 110 and second elongated magnetic core 130, so as to convey a magnetic field between first elongated magnetic core 110 and second elongated magnetic core 130. First elongated magnetic core 110 and second elongated magnetic core 130 may define magnetic poles. For example, the magnetic field at first elongated magnetic core 110 may be equal in intensity and opposite in polarity comparing to the magnetic field at second elongated magnetic core 130.

In some embodiments of the present invention, proximal surface 112 of first elongated magnetic core 110 and proximal surface 132 of second elongated magnetic core 130 may be substantially flat. First shorting bar 170 may connect at proximal surface 112 of first elongated magnetic core 110 and proximal surface 132 of second elongated magnetic core 130. Excitation coil 150 may be wrapped around first shorting bar 170. Current may pass through excitation coil 150 and induce a magnetic field in first elongated magnetic core 110 and second elongated magnetic core 130. Excitation coil 150 may be configured to keep view of sample 190 unobstructed.

In some embodiments of the present invention, distal surface of first elongated magnetic core 110 and distal surface of second elongated magnetic core 130 may be substantially flat. Excitation coil 150 may be elevated (e.g., may not come in contact with) sample 190. Electromagnet 100 may be configured to be leveled on a flat surface. For example, distal surfaces of the elongated magnetic cores may define a substantially flat plane, so that electromagnet 100 may have increase magnetic flux though sample 190.

In some embodiments of the present invention, first elongated magnetic core 110 may be substantially parallel to second elongated magnetic core 130, for ease of manufacturing and for uniformity of induced eddy currents.

In some embodiments of the present invention, first shorting bar 170 may be connect any part of first elongated magnetic core 110 and second elongated magnetic core 130. The position of first shorting bar 170 in relation to the magnetic cores may have a small difference on the resulting magnetic field. In some embodiments of the present invention first shorting bar 170 may be placed at edges of the magnetic cores so as not to obstruct view of sample 190.

Figure 2:
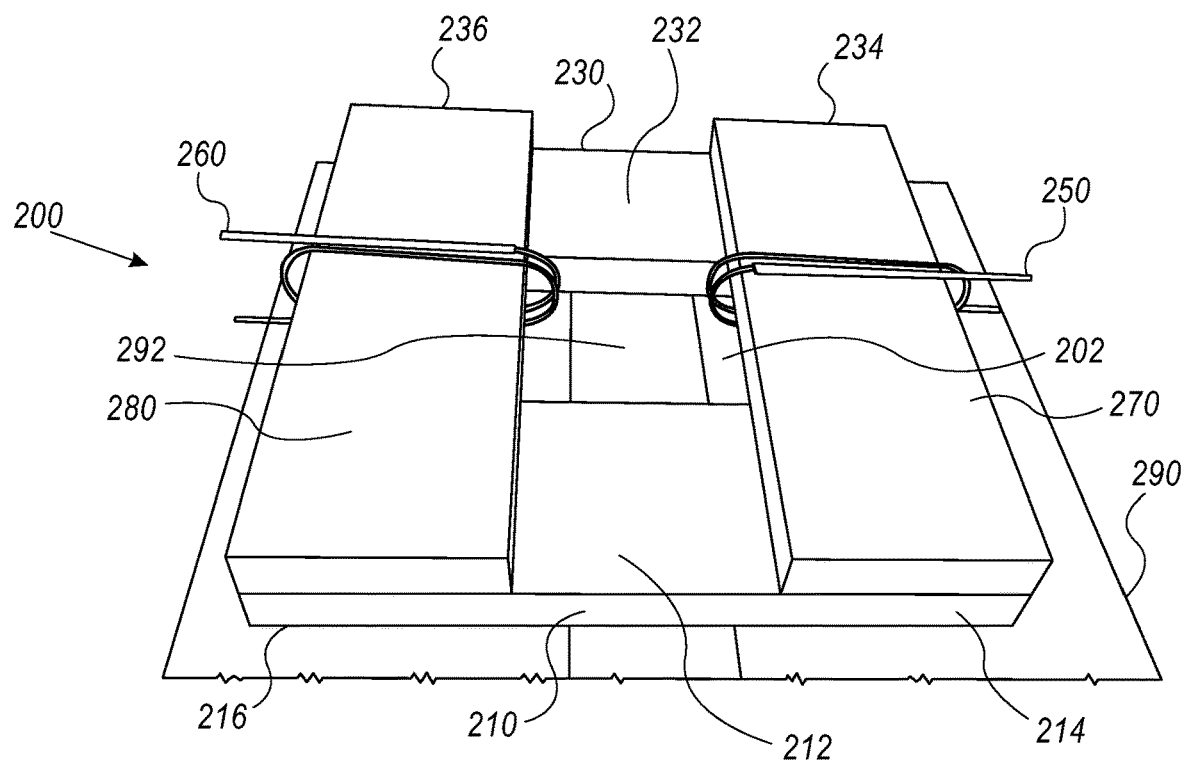
FIG. 2 is an electromagnet for a thermography system with two elongated magnetic cores, a first shorting bar connecting at a first end of the magnetic cores, and a second shorting bar connecting at a second end of the magnetic cores, in accordance with some embodiments of the present invention.

FIG. 2 is an electromagnet for a thermography system with two elongated magnetic cores, a first shorting bar connecting at a first end of the magnetic cores, and a second shorting bar connecting at a second end of the magnetic cores, in accordance with some embodiments of the present invention. Electromagnet 200 may comprise first elongated magnetic core 210 and second elongated magnetic core 230. First elongated magnetic core 210 may be spaced apart from second elongated magnetic core 230, so that gap 202 may form between first elongated magnetic core 210 and second elongated magnetic core 230.

In some embodiments of the present invention, first shorting bar 270 may connect substantially at first end 214 of first elongated magnetic core 210 and first end 234 of second elongated magnetic core 230. Second shorting bar 280 may connect substantially at second end 216 of first elongated magnetic core 210 and second end 236 of second elongated magnetic core 230. First shorting bar 270 and second shorting bar 280 may short first elongated magnetic core 210 and second elongated magnetic core 230, so as to convey a magnetic field between first elongated magnetic core 210 and second elongated magnetic core 230.

In some embodiments of the present invention, excitation coil 250 may be wrapped around first shorting bar 270. Second excitation coil 260 may be wrapped around second shorting bar 280. First excitation coil 250 may be wrapped in an opposite polarity (e.g., opposite looping direction) compared to second excitation coil 260. For example, a looping direction of first excitation coil 250 may be opposite to a looping direction of second excitation coil 260. When current flows through first excitation coil 250 and second excitation coil 260, electromagnet 200 may define a magnetic dipole. E.g., first elongated magnetic core 210 and second elongated magnetic core 230 may define magnetic poles. The magnetic field at first elongated magnetic core 210 may be equal in intensity and opposite in polarity comparing to the magnetic field at second elongated magnetic core 230.

In some embodiments of the present invention, excitation coils 250 and 260 may be configured to keep view of sample 290 unobstructed.

In some embodiments of the present invention, excitation coils 250 and 260 may be wrapped separately around shorting bars 270 and 280 respectively. For example, separate wires may be used to wrap excitation coils 260 and 260. In some embodiments of the present invention, a wire may be used to wrap excitation coils 250 and 260 in serial around shorting bars 270 and 280 respectively. For example, a wire may wrap first coil 250 around shorting bar 270 and serially wrap second coil 260 around shorting bar 280. Additionally or alternatively, a wire may wrap excitation coils 250 and 260 in parallel around shorting bars 270 and 280. In some embodiments of the present invention, first excitation coil 250 and second excitation coil 260 may be connected in serial. In some embodiments of the present invention, first excitation coil 250 and second excitation coil 260 may be connected in parallel.

In some embodiments of the present invention, first elongated magnetic core 210 may be substantially parallel to second elongated magnetic core 230, for ease of manufacturing and for uniformity of induced eddy currents.

Figure 3:
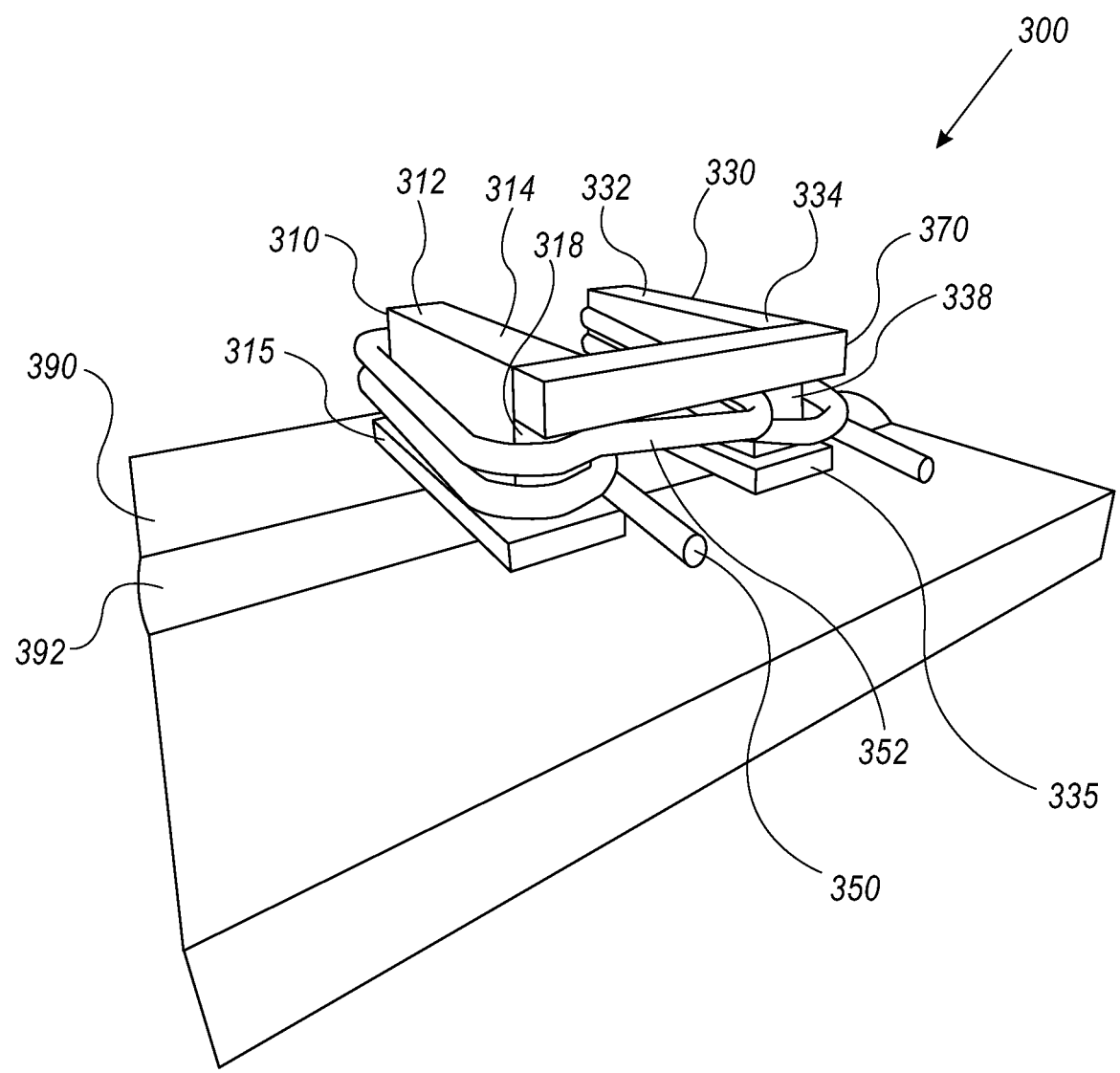
FIG. 3 is an electromagnet for a thermography system with two elongated magnetic cores and a first shorting bar connecting at a first end of the magnetic cores, wherein an excitation coil is wrapped around the magnetic cores, in accordance with some embodiments of the present invention.

FIG. 3 is an electromagnet for a thermography system with two elongated magnetic cores and a first shorting bar connecting at a first end of the magnetic cores, wherein an excitation coil is wrapped around the magnetic cores, in accordance with some embodiments of the present invention. Electromagnet 300 may comprise first elongated magnetic core 310 and second elongated magnetic core 330. First elongated magnetic core 310 may be spaced apart from second elongated magnetic core 330, so that gap 302 may form between first elongated magnetic core and second elongated magnetic core.

In some embodiments of the present invention, first shorting bar 370 may connect substantially at first end 314 of first elongated magnetic core 310 and first end 334 of second elongated magnetic core 330. First shorting bar 370 may short first elongated magnetic core 310 and second elongated magnetic core 330, so as to convey a magnetic field between first elongated magnetic core 310 and second elongated magnetic core 330.

In some embodiments of the present first shorting bar 370 may connect at first end 314 of first elongated magnetic core 310 and first end 334 of second elongated magnetic core 330.

In some embodiments of the present a second shorting bar may connect substantially at second end 312 of first elongated magnetic core 310 and second end 332 of second elongated magnetic core 330. The second shorting bar may short first elongated magnetic core 310 and second elongated magnetic core 330, so as to convey a magnetic field between first elongated magnetic core 310 and second elongated magnetic core 330.

In some embodiments of the present second shorting bar may connect at second end 312 of first elongated magnetic core 310 and second end 332 of second elongated magnetic core 330.

In some embodiments of the present invention, first shorting bar 370 may connect at first lateral surface 318 of first elongated magnetic core 310 and first lateral surface 338 of second elongated magnetic core 330. First excitation coil 350 may be wrapped around first elongated magnetic core 310 along an axis substantially orthogonal to a distal surface of first elongated magnetic core 310. First excitation coil 350 may be wrapped around second elongated magnetic core 330 along an axis substantially orthogonal to a distal surface of second elongated magnetic core 330.

In some embodiments of the present invention, the second shorting bar may connect at a second lateral surface of first elongated magnetic core 310 and second lateral surface of second elongated magnetic core 330.

In some embodiments of the present invention, first excitation coil 350 may be wrapped around first elongated magnetic core 310 in an opposite polarity (e.g., opposite looping direction) compared to second elongated magnetic core 330. For example, a looping direction of first excitation coil 350 around first elongated magnetic core 310 may be opposite to a looping direction of first excitation coil 350 around second elongated magnetic core 330. When current flows through first excitation coil 350, electromagnet 300 may define a magnetic dipole. E.g., first elongated magnetic core 310 and second elongated magnetic core 330 may define magnetic poles. For example, the magnetic field at first elongated magnetic core 310 may be equal in intensity and opposite in polarity comparing to the magnetic field at second elongated magnetic core 330. The wrapping of first excitation coil 370 around first elongated magnetic core 310 and second elongated magnetic core 330 may increase the coupling coefficient k.

In some embodiments of the present invention, a portion of the first excitation coil 352 that passes between first elongated magnetic core 310 and second elongated magnetic core 330 may be substantially parallel to first shorting bar 370.

In some embodiments of the present invention, first excitation coil 350 may be configured to keep view of sample 390 unobstructed.

In some embodiments of the present invention, distal surface of first elongated magnetic core 310 and distal surface of second elongated magnetic core 330 may be substantially flat. For example, first elongated magnetic core 310 may comprise a plate (e.g., additional magnetic core shaped like a plate) at the distal surface of first elongated magnetic core 310. Second elongated magnetic core 320 may comprise a plate at the distal surface of second elongated magnetic core 330. First Excitation coil 350 may be elevated (e.g., may not come in contact with) sample 390. Electromagnet 300 may be configured to be leveled on a flat surface. For example, distal surfaces of the elongated magnetic cores may define a substantially flat plane, so that electromagnet 300 may increase magnetic flux into sample 390.

In some embodiments of the present invention, wrapping first excitation coil 350 around first elongated magnetic core 310 and second elongated magnetic core 330 may yield a value of k close to 1. Stray magnetic flux may be decreased, so that the unwanted electromagnetic interference is decreased as well.

In some embodiments of the present invention, first edition coil 350 may be wrapped around a portion of the elongated magnetic cores. E.g., excitation coil 350 may leave portions of the elongated magnetic cores exposed in order to prevent magnetic saturation. First excitation coil 350 may leave proximal portions of the magnetic cores exposed in order to decrease magnetic saturation.

In some embodiments of the present invention, first excitation coil 350 may be wrapped around distal portions of the elongated magnetic cores for reducing stray magnetic flux (e.g., reducing the magnetic flux going to the proximal part of the magnetic cores, that may cause EMI).

In some embodiments of the present invention, first elongated magnetic core 310 and second elongated magnetic core 330 may have separate excitation coils (e.g., made of different wires, and/or wrapped separately). For example, separate wires may be used to wrap excitation coils around first elongated magnetic core 310 and second elongated magnetic core 330 respectively. In some embodiments of the present invention, an excitation coil wrapped around first elongated magnetic core 310 may be connected in serial to an excitation coil wrapped around second elongated magnetic core 330. In some embodiments of the present invention, an excitation coil wrapped around first elongated magnetic core 310 may be connected in parallel to an excitation coil wrapped around second elongated magnetic core 330.

Figure 4:
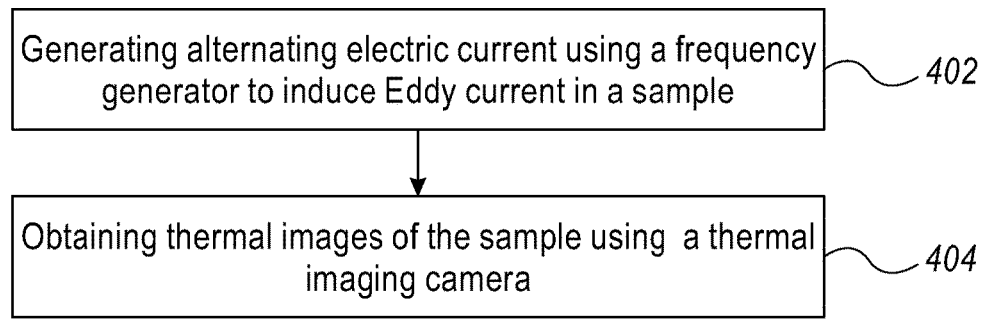
FIG. 4 is a flowchart of a method for thermographic imaging using a thermography system, in accordance with some embodiments of the present invention.

FIG. 4 is a flowchart of a method for thermographic imaging using a thermography system, in accordance with some embodiments of the present invention. The method for thermographic imaging may involve a frequency generator connected to an excitation coil in an electromagnet. The electromagnet may comprise an elongated first magnetic core and an elongated second magnetic core, at least a first shorting bar. The shorting bar may connect the first and second magnetic cores substantially at a first end of the first and second magnetic cores. The method for thermographic imaging may include generating alternating electric current using a frequency generator to induce eddy current in a sample 402.

The alternating current may pass through the excitation coil and induce a magnetic field, the magnetic field may induce eddy currents in a sample. The sample may be heated due to the induced eddy current. According to some embodiments of the present invention, the method for thermographic imaging may include obtaining thermal images of the sample using a thermal imaging camera 404. The thermal images may then be analyzed to detect defects in the sample.

Figure 5:
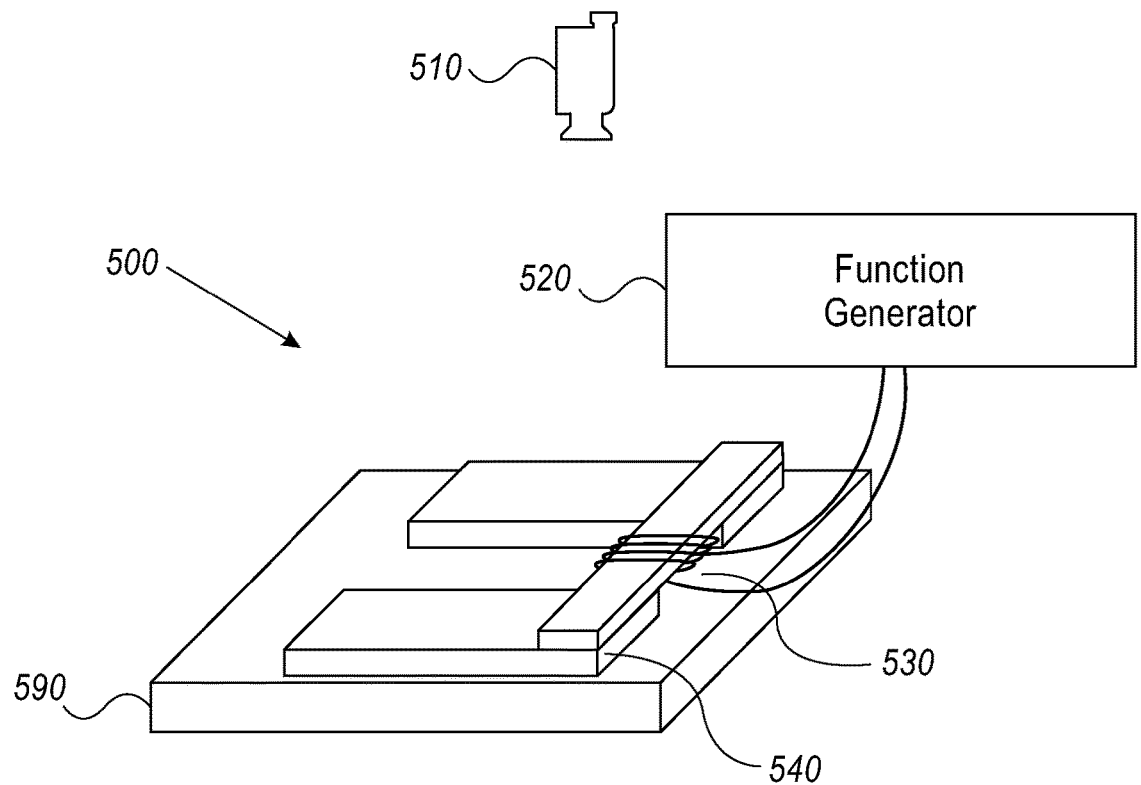
FIG. 5 is a thermography system, in accordance with some embodiments of the present invention.

FIG. 5 is a thermography system, in accordance with some embodiments of the present invention. Thermography system 500 may include function generator 520 connected to excitation coil 530. Excitation coil 530 may be wrapped around parts of electromagnet 540. Current passing through excitation coil 530 may induce eddy currents in sample 590. The induced eddy currents in sample 590 may heat sample 590. Thermal camera 510 may take a thermal image of sample 590. The thermal image of sample 590 may be analyzed to detect defects in in sample 590.

In some embodiments of the present invention thermal camera 510 may be an infra-red camera. Thermal camera 510 may be connected to a computing system for storing, viewing and analyzing thermal images of sample 590. Thermal camera 510 may be connected wirelessly to a computer. E.g., via Bluetooth, Wi-Fi, and other wireless communication technologies. Thermal camera 510 may comprise a computer (e.g., controller) and a display configured to view, analyze and store thermal images of sample 590.

In some embodiments of the present invention, thermography system 500 may include algorithms and functions for analyzing thermal images of sample 590. Thermography system 500 may connect to a remote location for analyzing, viewing and storing thermal images of sample 590. For example, thermography system 500 may, connect to remote storage units (e.g., data center, cloud storage, etc.) for storing thermal images of sample 590 and analysis of thermal images of sample 590. Thermography system 500 may connect to a remote computer (e.g., server, cloud, etc.) for analyzing and storing thermal images of sample 590. Thermography system 500 may be configured to have a remote access, so that a user of thermography system 500 may access and control thermography system 500 (e.g., remote access program with web connectivity). Thermography system 500 may include a memory device for storing thermal images and analysis of thermal images of sample 590. E.g., thermography system 500 may include a flash memory, hard drive, and similar data storage devices.

Different embodiments are disclosed herein. Features of certain embodiments may be combined with features of other embodiments. Thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A thermography system, the system comprising:
   a thermal imaging camera;
   a frequency generator; and
   an electromagnet comprising an elongated first magnetic core and an elongated second magnetic core, at least a first shorting bar, and at least a first excitation coil connected to the frequency generator, wherein
   the first shorting bar connects the first and second magnetic cores substantially at a first end of the first and second magnetic cores, and wherein the first excitation coil is wrapped around the first magnetic core along an axis substantially orthogonal to a distal surface of the first magnetic core, and wherein the first excitation coil is wrapped around the second magnetic core along an axis substantially orthogonal to a distal surface of the second magnetic core.

2. The thermography system of claim 1, wherein the imaging camera is an infra-red camera.

3. A method for thermographic imaging using a thermography system, the method comprising:
   generating alternating electric current using a frequency generator to induce Eddy current in a sample, the frequency generator connected to a first excitation coil in an electromagnet, the electromagnet comprising an elongated first magnetic core and an elongated second magnetic core, at least a first shorting bar, the shorting bar connecting the first and second magnetic cores substantially at a first end of the first and second magnetic cores, the first excitation coil wrapping around the first magnetic core along an axis substantially orthogonal to a distal surface of the first magnetic core, and around the second magnetic core along an axis substantially orthogonal to a distal surface of the second magnetic core; and
   obtaining thermal images of the sample using a thermal imaging camera.

* * * * *